(12) United States Patent
Stahmann et al.

(10) Patent No.: US 7,215,992 B2
(45) Date of Patent: May 8, 2007

(54) METHOD FOR ISCHEMIA DETECTION BY IMPLANTABLE CARDIAC DEVICE

(75) Inventors: Jeffrey E. Stahmann, Ramsey, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 540 days.

(21) Appl. No.: 10/669,168

(22) Filed: Sep. 23, 2003

(65) Prior Publication Data

US 2004/0133247 A1 Jul. 8, 2004

Related U.S. Application Data

(63) Continuation-in-part of application No. 09/999,255, filed on Oct. 31, 2001, now Pat. No. 6,937,901, and a continuation-in-part of application No. 10/436,876, filed on May 12, 2003, now Pat. No. 7,069,070.

(51) Int. Cl.
*A61B 5/468* (2006.01)

(52) U.S. Cl. .................................... 600/515

(58) Field of Classification Search ................ 600/508, 600/509, 513–518, 521; 607/14, 27, 28
See application file for complete search history.

(56) References Cited

U.S. PATENT DOCUMENTS

| | | | |
|---|---|---|---|
| 4,777,960 A | 10/1988 | Berger et al. |
| 4,945,909 A | 8/1990 | Fearnot et al. |
| 5,014,698 A | 5/1991 | Cohen |
| 5,025,786 A | 6/1991 | Siegel |
| 5,063,927 A | 11/1991 | Webb et al. |
| 5,197,467 A | 3/1993 | Steinhaus et al. |
| 5,199,428 A | 4/1993 | Obel et al. |
| 5,269,301 A | 12/1993 | Cohen |
| 5,271,395 A | 12/1993 | Wahlstrand et al. |
| 5,273,034 A | 12/1993 | Nilsson |
| 5,303,702 A | 4/1994 | Bonnet et al. |
| 5,360,436 A | 11/1994 | Alt et al. |
| 5,423,870 A | 6/1995 | Olive et al. |
| 5,480,412 A | 1/1996 | Mouchawar et al. |
| 5,535,752 A | 7/1996 | Halperin et al. |
| 5,755,671 A | 5/1998 | Albrecht et al. |
| 6,128,526 A | 10/2000 | Stadler et al. |
| 6,678,547 B2 | 1/2004 | Carlson et al. |

(Continued)

OTHER PUBLICATIONS

Bigger, JR., J. T., "Spectral Analysis of R-R Variability to Evaluate Autonomic Physiology and Pharmacology and to Predict Cardiovascular Outcomes in Humans", *Diagnostic Evaluation, Part XI, Chapter 101*, 1151-1170.

(Continued)

*Primary Examiner*—Mark Bockelman
(74) *Attorney, Agent, or Firm*—Schwegman, Lundberg, Woessner, & Kluth, P.A.

(57) ABSTRACT

A cardiac device in which heart rate variability is computed in order to detect changes indicative of cardiac ischemia. In the case where the device is a pacemaker, the device may alter its pacing mode to limit the rate at which paces are delivered when ischemia is detected. Examples of such pacing mode alterations include discontinuing of rate-adaptive pacing, modification of the responsiveness of the rate-adaptive algorithm, or the decreasing of the maximum allowable pacing rate.

21 Claims, 2 Drawing Sheets

U.S. PATENT DOCUMENTS

| | | |
|---|---|---|
| 6,937,901 B2 | 8/2005 | Zhu et al. |
| 7,062,314 B2 * | 6/2006 | Zhu et al. .................. 600/515 |
| 7,069,070 B2 | 6/2006 | Carlson et al. |
| 2003/0060854 A1 | 3/2003 | Zhu |
| 2004/0133247 A1 | 7/2004 | Stahmann et al. |
| 2004/0158295 A1 | 8/2004 | Dyjach et al. |
| 2004/0230214 A1 | 11/2004 | Carlson et al. |
| 2005/0090719 A1 | 4/2005 | Scheiner et al. |
| 2005/0240237 A1 | 10/2005 | Zhu et al. |
| 2005/0261741 A1 | 11/2005 | Libbus et al. |
| 2006/0195038 A1 | 8/2006 | Carlson et al. |

OTHER PUBLICATIONS

Kochiadakis, G. F., "Autonomic nervous system activity before and during episodes of myocardial ischemia in patients with stable coronary artery disease during daily life", *Pacing Clin Electrophysiol., 23(12)*, (Dec. 2000), 2030-9.

Lanza, G. A., et al., "Usefulness of the Addition of Heart Rate Variability to Holter Monitoring in Predicting In-Hospital Cardiac Events in Patients With Unstable Angina Pectoris", *The American Journal of Cardiology, 80(3)*, (Aug. 1, 1997), 263-267.

"Heart rate variability: standards of measurement, physiological interpretation and clinical use. Task Force of the European Society of Cardiology and the North American Society of Pacing and Electrophysiology", *Circulation, 93(5)*, (Mar. 1, 1996), 1043-1065.

Vardas, P. E., et al., "Spectral analysis of heart rate variability before and during episodes of nocturnal ischaemia in patients with extensive coronary artery disease", *Eur Heart J., 17(3)*, (Mar. 1996), 388-93.

\* cited by examiner

METHOD FOR ISCHEMIA DETECTION BY IMPLANTABLE CARDIAC DEVICE

CROSS-REFERENCE TO RELATED APPLICATION(S)

This application is a continuation-in-part of U.S. patent application Ser. No. 09/999,255, filed on Oct. 31, 2001 now U.S. Pat. No. 6,937,901 and Ser. No. 10/436,876, filed May 12, 2003 now U.S. Pat. No. 7,069,070, the specifications of which are incorporated herein by reference

FIELD OF THE INVENTION

This invention pertains to systems and methods for cardiac monitoring and rhythm management. In particular, the invention relates to implantable cardiac devices and their methods of operation.

BACKGROUND

Implantable cardiac devices are devices that monitor cardiac function and may also provide electrical stimulation to selected chambers of the heart in order to treat disorders of cardiac rhythm. Such cardiac devices include pacemakers, implantable cardioverter/defibrillators, cardiac resynchronization devices, and implantable cardiac monitoring devices. A pacemaker is a cardiac rhythm management device that paces the heart with timed pacing pulses. The term "pacemaker" as used herein, however, should be taken to mean both pacemakers and any device with a pacing functionality, such as an implantable cardioverter/defibrillator with a pacemaker incorporated therein.

The most common condition for which pacemakers are used is the treatment of bradycardia where the intrinsic heart rate is too slow. The two most common causes of ventricular bradycardia are AV block and sick sinus syndrome. Permanent pacing for bradycardia is indicated in patients with symptomatic bradycardia of any type as long as it is likely to be permanent or recurrent and is not associated with a transient condition from which the patient may recover. In chronotropically competent patients (i.e., those patients whose atrial rhythm is responsive to metabolic demand) in need of ventricular pacing, atrial triggered modes such as DDD or VDD are desirable because they allow the pacing to track the physiologically normal atrial rhythm, which causes cardiac output to be responsive to the metabolic needs of the body.

In pacemaker patients who are chronotropically incompetent (e.g., sinus node dysfunction) or in whom atrial tracking modes such as DDD and VDD are contraindicated due to atrial arrhythmias, the heart rate is dictated solely by the pacemaker in the absence of faster intrinsic cardiac activity. That pacing rate is determined by the programmed escape intervals of the pacemaker and is referred to as the lower rate limit or LRL. Pacing the heart at a fixed rate as determined by the LRL setting of the pacemaker, however, does not allow the heart rate to increase with increased metabolic demand. Cardiac output is determined by two factors, the stroke volume and heart rate, with the latter being the primary determinant. Although stroke volume can be increased during exercise (e.g., due to increased venous return and increased myocardial contractility), the resulting increase in cardiac output is usually not sufficient to meet the body's metabolic needs unless the heart rate is also increased. If the heart is paced at a constant rate, severe limitations are imposed upon the patient with respect to lifestyle and activities. It is to overcome these limitations and improve the quality of life of such patients that rate-adaptive pacemakers have been developed. In a rate-adaptive pacemaker, the patient's metabolic demand is estimated with an exertion level sensor such as an accelerometer or minute-ventilation sensor. The sensed exertion level is then mapped to a sensor-indicated rate that becomes the lower rate limit for the pacemaker.

Rate-adaptive pacing is generally considered to be contraindicated for patients with known coronary artery disease (CAD) since the increase in heart rate brought about by rate-adaptive pacing also increases the oxygen demand of the heart. If the heart becomes ischemic due to insufficient blood flow in the face of increased oxygen demand, chest pain (angina pectoris) or triggering of an arrhythmia may result. For the same reasons, atrial tracking ventricular pacing modes may also be contraindicated in certain patients where cardiac ischemia results from atrial tracking pacing at high rates. Some pacemaker patients, however, may have undetected CAD with asymptomatic silent ischemia or may develop CAD subsequent to pacemaker implantation. It would be beneficial if the pacemaker could detect episodes of cardiac ischemia in those patients in order to provide that information to a clinician and/or automatically adjust the operation of the pacemaker.

Patients may also benefit from implantable devices that monitor cardiac function, but do not deliver therapy. These devices monitor cardiac rhythm or other parameters relating to cardiac function such as blood pressure or activity. The information gathered by the implantable device may then be communicated to a clinician for use in evaluating, and when appropriate treating, the patient.

SUMMARY

The present invention relates to a technique for detecting cardiac ischemia which may be implemented in an implantable cardiac device such as a pacemaker or other cardiac rhythm management device. Such a detected change may then be logged as a clinically significant event with a recorded electrogram later downloaded to a clinician for analysis via an external programmer. In the case of a pacemaker, detection of ischemia may also be used to automatically adjust the pacing rate in pacing modes that allow the pacing rate to change with metabolic demand. For example, in atrial tracking pacing modes, the maximum tracking rate can be decreased so that the ventricles are paced at that rate in keeping with the myocardial blood supply even if the intrinsic atrial rate is higher. In rate-adaptive pacing modes, where an escape interval for pacing a heart chamber is adjusted in order to pace the chamber at a sensor-indicated rate based upon a sensed exertion level, the maximum allowable sensor-indicated rate can be decreased. The response factor of the rate response curve used for rate-adaptive pacing can also be adjusted to map a given exertion level to a lower sensor-indicated rate if cardiac ischemia is detected.

DETAILED DESCRIPTION

The present invention relates to a technique for detecting ischemia in a cardiac rhythm management device. Several studies have found that acute changes in heart rate variability (HRV) occur shortly before and during ischemic events. (See, e.g., "Autonomic nervous system activity before and during episodes of myocardial ischemia in patients with stable coronary artery disease during daily life," Kochiadakis et al., *Pacing Clin Electrophysiol* 2000 December; 23(12):2030–9; "Spectral analysis of heart rate variability before and during episodes of nocturnal ischaemia in patients with extensive coronary artery disease," Vardas et al., *Eur Heart J* 1996 March; 17(3):388–93; Comment in: *Eur Heart J.* 1996 March;17(3):331–3; "Usefulness of the addition of heart rate variability to Holter monitoring in predicting in-hospital cardiac events in patients with unstable angina pectoris," Lanza et al., *Am J Cardiol Aug.* 1, 1997; 80(3):263–7.) In an exemplary embodiment of the invention, a patient's atrial rate is monitored, specific HRV measurements are calculated, and changes in the HRV measurements and possibly other physiological metrics are then identified to predict and identify acute ischemic events. What follows is a description of the technique as well as of the hardware components and operating modes of a device in which the method may be implemented.

1. Exemplary Hardware Platform

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
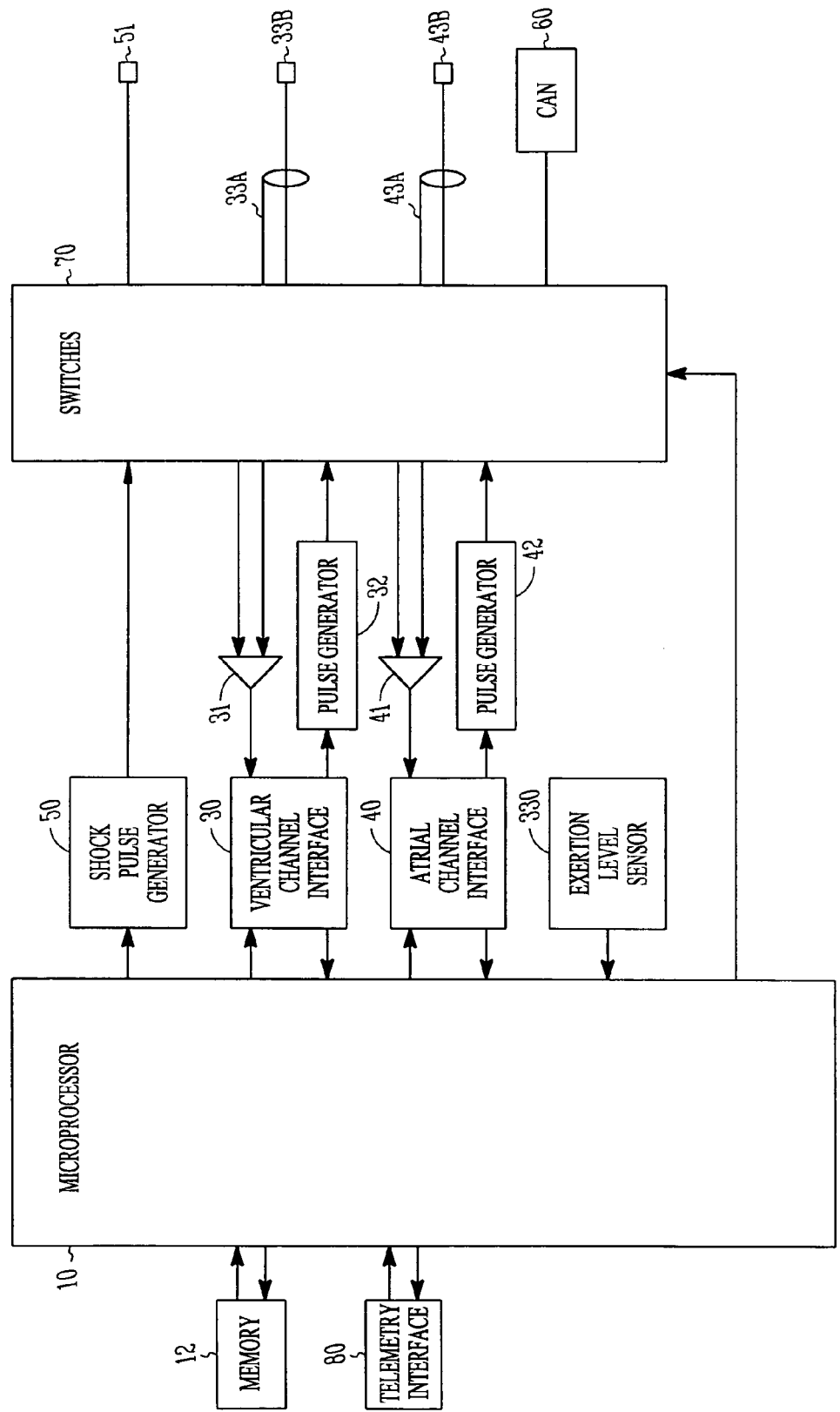
FIG. 1 is a block diagram of an implantable cardiac device.

The present invention may be incorporated into any cardiac rhythm management device including pacemakers having a number of different pacing configurations, such as those used for multi-site pacing configurations in delivering resynchronization therapy. For illustrative purposes, however, a block diagram of a dual-chamber pacemaker (i.e., one that senses and/or paces the atria and ventricles) is shown in FIG. 1. The controller of the pacemaker is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals.

The device is equipped with multiple electrodes, sensing amplifiers, and pulse generators which can be configured as channels for pacing and/or sensing selected heart chambers. A MOS switch matrix 70 controlled by the microprocessor is used to configure a sensing or pacing channel by switching selected electrodes to the input of a sense amplifier or to the output of a pulse generator. The switch matrix 70 allows the device to employ either bipolar sensing/pacing using two closely spaced electrodes of a lead or unipolar sensing/pacing using one of the electrodes of a lead and the can 60 as a reference electrode. In the device illustrated in FIG. 1, an atrial sensing/pacing channel is configured with ring electrode 43a, tip electrode 43b, sense amplifier 41, pulse generator 42, and an atrial channel interface 40 which communicates bidirectionally with a port of microprocessor 10. A ventricular sensing/pacing channel is similarly configured with ring electrode 33a, tip electrode 33b, sense amplifier 31, pulse generator 32, and a ventricular channel interface 30. The sense amplifiers and pulse generators are interfaced to the controller by channel interfaces which may include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or changing the pacing pulse amplitude.

The controller 10 controls the overall operation of the device in accordance with programmed instructions stored in memory and with information derived from the sensing channels. The voltages sensed by the sensing electrodes are electrogram signals that are analogous to a surface ECG and provide a temporal record of cardiac depolarization and repolarization that occurs during either intrinsic or paced beats. The electrogram signals can be digitized and recorded by the controller and then either transmitted via a telemetry link 80 to an external programmer or stored for later transmission. The patient's cardiac activity may thus be observed in real-time or over a selected historical period. The sensing circuitry of the pacemaker generates atrial and ventricular senses when voltages sensed by the electrodes of a particular channel exceed a specified threshold. A ventricular sense would correspond to an R wave on an ECG, and an atrial sense would correspond to a P wave. The controller 10 interprets sense signals from the sensing channels in order to detect arrhythmias and to control the delivery of paces in accordance with a pacing algorithm that employs such senses to trigger or inhibit pacing. An exertion level sensor 330 (e.g., an accelerometer or a minute ventilation sensor) enables the controller to adapt the pacing rate in accordance with changes in the patient's physical activity.

When an arrhythmia is detected, the controller may cause appropriate therapy to be delivered. For this purpose, the device in FIG. 1 also includes a shock pulse generator 50 interfaced to the controller for delivering cardioversion/defibrillation shocks to the heart via a selected pair of electrodes such as a coil electrode 51 and the can 60. The device may also deliver pacing therapy in accordance with an anti-tachycardia pacing (ATP) protocol in order to treat certain arrhythmias.

2. Measurement of Heart Rate Variability to Detect Cardiac Ischemia

Increased activity of the sympathetic nervous system is associated with metabolic stress and has been found to occur both shortly before and during an episode of cardiac ischemia. One means by which increased sympathetic activity may be detected is via spectral analysis of heart rate variability. Heart rate variability refers to the variability of the time intervals between successive heart beats during a sinus rhythm and is primarily due to the interaction between the sympathetic and parasympathetic arms of the autonomic nervous system. Spectral analysis of heart rate variability involves decomposing a signal representing successive beat-to-beat intervals into separate components representing the amplitude of the signal at different oscillation frequencies. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity. An LF/HF ratio which exceeds a specified threshold value may be taken as an indicator that cardiac ischemia is occurring or about to occur.

A cardiac rhythm management device can be programmed to determine the LF/HF ratio by analyzing data received from its ventricular sensing channels. (See, e.g., U.S. patent application Ser. No. 09/999,255, filed on Oct. 31, 2001 and hereby incorporated by reference). The intervals between successive ventricular senses, referred to as RR intervals, can be measured and collected for a period of time or a specified number of beats. In order to derive a signal representing heart rate variability during a sinus rhythm, ectopic ventricular beats (i.e., premature ventricular contractions or PVCs) can be detected by monitoring whether a P wave precedes each R wave, with the RR intervals before and after the PVC changed to an interpolated or otherwise filtered value. The resulting series of RR interval values is then stored as a discrete signal. The signal can be used directly as indexed by heartbeat such that each value of the signal represents an RR interval for a particular heartbeat. Preferably, however, the signal is resampled at a specified sampling frequency in order to equalize the time intervals between signal values and thus convert the signal into a discrete time signal, where the sampling frequency is selected to meet the Nyquist criterion with respect to the frequencies of interest. In any case, the RR interval signal can then be analyzed to determine its energies in the high and low frequency bands as described above.

Figure 2:
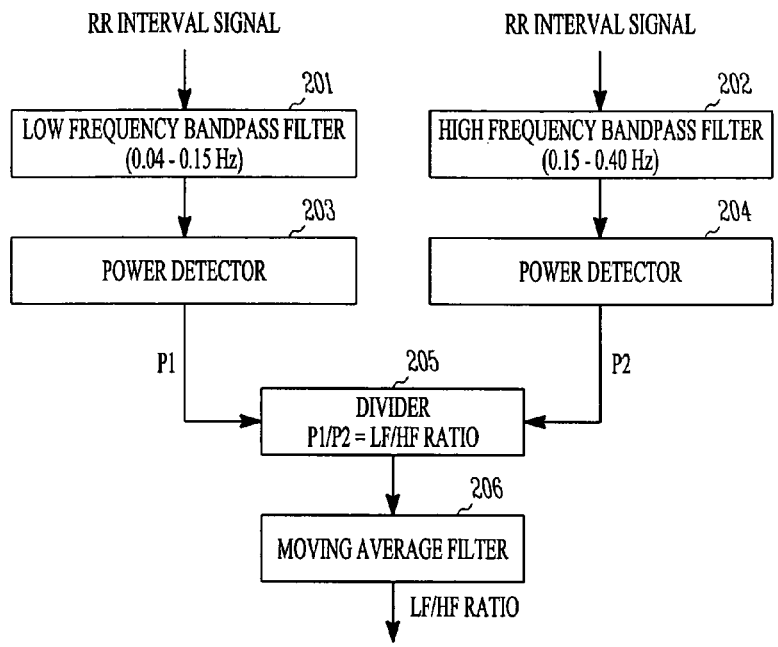
FIG. 2 is a block diagram of exemplary components for computing the LF/HF ratio.

Spectral analysis of an RR interval signal can be performed directly in the frequency domain using time frequency analysis such as discrete Fourier transform or autoregression techniques. Frequency domain analysis is computationally intensive, however, and may not be practical in an implantable device. A time-domain technique for determining the high and low frequency components of the signal is therefore preferably used. FIG. 2 illustrates the functional components of an exemplary system for doing this that can be implemented as code executed by the controller and/or dedicated hardware components. The RR interval signal obtained as described above is input to both a low band digital filter 201 and a high band digital filter 202. The low band filter 201 is a bandpass filter with a passband corresponding to the LF band (e.g., 0.04 to 0.15 Hz), while the high band filter 202 is a bandpass filter with a passband corresponding to the HF band (e.g., 0.15 to 0.40 Hz). The outputs of filters 201 and 202 are then input to power detectors 203 and 204, respectively, in order to derive signals proportional to the power of the RR interval signal in each of the LF and HF bands. Power detection may be performed, for example, by squaring the amplitude of the signal and integrating over a specified average time. The output of power detector 203 is thus a signal P1 that represents the power of the RR interval signal in the LF band, and the output of power detector 204 is a signal P2 representing the power in the HF band. The signals P1 and P2 are next input to a divider 205 that computes the quantity S1/S2 which equals the LF/HF ratio. The LF/HF ratio is then input to a moving average filter 206 that computes an average value for the ratio over a specified period (e.g., 5 minutes). An updated LF/HF ratio may be computed in this manner on a beat-to-beat basis.

In the above description, heart rate variability was derived from the RR interval signal during normal sinus rhythm. It should also be appreciated that, if normal sinus rhythm is present, the RR interval is equivalent to the interval between successive atrial senses. As used herein, therefore, the term RR interval should be regarded as the interval between heart beats during sinus rhythm whether the beats are atrial or ventricular. Also, as an alternative to time-domain filtering, a statistical method of estimating the LF/HF ratio may be employed as described in U.S. patent application Ser. No. 10/436,876 filed May 12, 2003 and herein incorporated by reference.

The device may thus be programmed to detect ischemia when the computed LF/HF ratio exceeds a predetermined threshold value or a predetermined rate of change. The predetermined threshold and rate of change values may be fixed or may be determined by the device based upon previous measurements. Additional specificity to the criteria for detecting ischemia may be obtained by analyzing ventricular electrogram morphology as described in U.S. patent application Ser. No. 09/962,852 filed Sep. 25, 2001 and herein incorporated by reference.

3. Adjustment in Pacemaker Operation Triggered by Ischemia Detection

If a change in heart rate variability indicative of ischemia is detected, the change may be logged as a clinically significant event in the pacemaker's memory. The event log and/or the recorded electrogram exhibiting the ischemia may then be later downloaded to a clinician for analysis via an external programmer. The clinician is then able to use this information in making subsequent treatment decisions. Detection of ischemia may also be used to automatically adjust the pacing rate in pacing modes that allow the pacing rate to change with metabolic demand. In an atrial tracking mode, for example, one or both ventricles are paced after expiration of a programmed atrio-ventricular interval if no preceding ventricular sense occurs, where the atrio-ventricular interval begins with an atrial sense. The pacing of the ventricles thus tracks the intrinsic atrial rate which, in a chronotropically competent patient, is responsive to metabolic demand. For safety reasons, a maximum tracking rate is usually programmed into an atrial tracking mode that limits the rate at which the ventricles can be paced regardless of the atrial rate. When ischemia is detected by the pacemaker, the controller may be programmed to automatically decrease the maximum tracking rate so that the ventricles are paced at that rate in keeping with the myocardial blood supply even if the intrinsic atrial rate is higher. Decreasing of the maximum tracking rate may thus prevent exacerbation of the ischemia from pacing at too high a rate.

Figure 3:
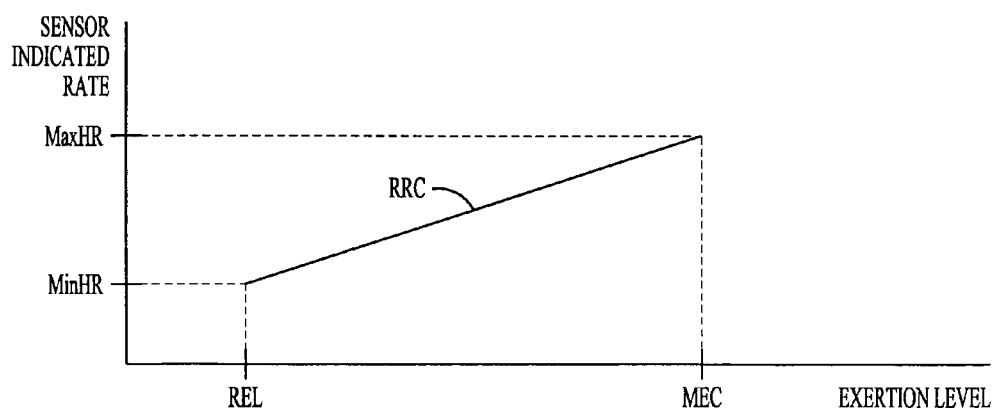
FIG. 3 is a diagram of a single-slope rate response curve.

Automatic adjustment of the maximum pacing rate when cardiac ischemia is detected may also be employed in rate-adaptive pacing. Rate-adaptive pacemakers modulate the ventricular and/or atrial escape intervals based upon measurements corresponding to physical activity and are applicable to situations in which atrial tracking modes cannot be used. In a rate-adaptive pacemaker operating in a ventricular pacing mode, the LRL is adjusted in accordance with exertion level measurements such as from an accelerometer or minute ventilation sensor in order for the heart rate to more nearly match metabolic demand. The adjusted LRL is then termed the sensor-indicated rate. The responsiveness of a rate-adaptive pacemaker is controlled in accordance with a rate-response curve RRC such as shown in FIG. 3. Other embodiments may use a dual-slope curve or a non-linear curve. A change in exertion level as determined from, for example, a minute ventilation measurement causes a proportional change in the sensor indicated rate in accordance with the slope of the curve, termed the response factor RF. The sensor indicated rate is then used as a lower rate limit (LRL) by the pacemaker to pace the heart in accordance with a programmed pacing mode, where the LRL is the rate at which the heart is paced in the absence of faster intrinsic activity. As shown in the figure, the rate response curve maps a resting exertion level REL to a minimum sensor indicated rate MinHR which corresponds to the minimum LRL that is to be used by the pacemaker. The maximum sensor indicated rate MaxHR is the maximum rate at which the pacemaker is allowed to pace the heart and is mapped to by the rate response curve from the maximum exertion level the patient is expected to be able to reach, referred to as the maximum exercise capacity MEC. When cardiac ischemia is detected, the controller may be programmed to either discontinue rate-adaptive pacing and revert to the programmed LRL setting or continue rate-adaptive pacing with a decreased maximum allowable sensor-indicated rate MaxHR. When rate-adaptive pacing is continued after detection of ischemia, the response factor of the rate response curve can also be adjusted to map a given exertion level to a lower sensor-indicated rate.

As found in studies on HRV and ischemia, changes to the LF/HF ratio can precede an ischemic event. As such the changes to the LF/HF ratio may be used to predict an imminent ischemia. Changes to the pacemaker behavior described above may thus be used to prevent the ischemic event. In addition, communication of the imminent event to the patient may allow the patient the change their behavior, such as reducing activity or stress, thereby precluding the ischemic event.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An implantable cardiac device, comprising:
   a sensing channel for sensing an electrogram signal and generating a chamber sense when the electrogram signal exceeds a specified threshold value;
   circuitry for measuring and collecting time intervals between successive chamber senses and storing the collected intervals as a discrete RR interval signal, filtering the RR interval signal into defined high and low frequency bands, and determining the signal power of the RR interval signal in each of the low and high frequency bands, referred to LF and HF, respectively; and,
   circuitry for computing an LF/HF ratio and detecting cardiac ischemia if the LF/HF ratio exceeds a predetermined ratio threshold value; and
   a controller for storing detection of cardiac ischemia.

2. The device of claim 1 further comprising;
   a pacing channel for pacing a cardiac chamber; and,
   wherein the controller is further programmed to deliver paces to the cardiac chamber in accordance with a programmed pacing mode.

3. The device of claim 2 wherein the controller is programmed to alter a rate at which paces are delivered after detecting ischemia.

4. The device of claim 2 further comprising an exertion level sensor and wherein the controller is further programmed to:
   sense an exertion level and map the sensed exertion level to a particular sensor-indicated rate with a rate-response curve, wherein the sensor-indicated rate is limited to a specified maximum sensor-indicated rate;
   adjust an escape interval in order to enforce the sensor-indicated rate; and,
   decrease the specified maximum sensor-indicated rate if a change in the LF/HF ratio indicative of cardiac ischemia is detected.

5. The device of claim 4 wherein the controller is further programmed to adjust the response factor of the rate-response curve so that a particular exertion level particular is mapped to a lower sensor-indicated rate if a change in the LF/HF ratio indicative of cardiac ischemia is detected.

6. The device of claim 2 further comprising:
   an exertion level sensor;
   wherein the controller is further programmed to pace the heart in a rate-adaptive pacing mode by sensing an exertion level, map the sensed exertion level to a particular sensor-indicated rate with a rate-response curve, and adjust an escape interval in order to enforce the sensor-indicated rate; and,
   wherein the controller is programmed to discontinue rate responsive pacing upon detection of ischemia.

7. The device of claim 2 wherein the paced heart chamber is a ventricle and the programmed pacing mode is an atrial tracking mode such that a ventricular pace is delivered after expiration of an atrio-ventricular interval without a ventricular sense, the atrio-ventricular interval being started by an atrial sense, and further wherein the controller is programmed to decrease a maximum tracking rate that limits the rate at which ventricular paces can be delivered in response to atrial senses if cardiac ischemia is detected.

8. The device of claim 2 wherein the controller is programmed to decrease a maximum rate at which paces are delivered upon detection of ischemia.

9. The device of claim 1 wherein the circuitry for computing an LF/HF ratio and detecting cardiac ischemia further comprises detecting ischemia if the LF/HF ratio exceeds a predetermined rate of change.

10. The device of claim 1 wherein the controller is further programmed to log a detection of cardiac ischemia as a clinically significant event.

11. The device of claim 1 wherein the controller is programmed to detect ischemia if the LF/HF ratio exceeds the specified threshold and if a change in a recorded electrogram indicative of cardiac ischemia is detected.

12. The device of claim 1 wherein the RR intervals are intervals between ventricular senses.

13. The device of claim 12 further comprising circuitry for detecting ectopic ventricular beats and filtering the RR intervals before and after such beats to derive the RR interval signal.

14. The device of claim 12 further comprising circuitry for resampling the RR interval signal to equalize the time intervals between values of the RR interval signal.

15. A method, comprising:
sensing an electrogram signal from an implanted electrode;
generating a chamber sense when the electrogram signal exceeds a specified threshold value;
collecting RR time intervals between successive chamber senses;
filtering the RR interval signal into defined high and low frequency bands;
determining the signal power of the RR interval signal in each of the low and high frequency bands, referred to LF and HF, respectively;
computing an LF/HF ratio;
detecting cardiac ischemia if the LF/HF ratio exceeds a predetermined ratio threshold value.

16. The method of claim 15 further comprising delivering paces to a cardiac chamber in accordance with a programmed pacing mode and rate.

17. The method of claim 16 wherein the pacing rate is altered after detecting ischemia.

18. The method of claim 16 wherein the maximum rate at which paces are delivered upon detection of ischemia is decreased.

19. The method of claim 15 further comprising logging detection of cardiac ischemia as a clinically significant event.

20. The method of claim 15 further comprising:
sensing an exertion level and mapping the sensed exertion level to a particular sensor-indicated rate with a rate-response curve, wherein the sensor-indicated rate is limited to a specified maximum sensor-indicated rate;
adjusting an escape interval used to deliver paces in order to enforce the sensor-indicated rate; and,
decreasing the specified maximum sensor-indicated rate if a change in the LF/HF indicative of cardiac ischemia is detected.

21. The method of claim 20 wherein the response factor of the rate-response curve is adjusted so that a particular exertion level particular is mapped to a lower sensor-indicated rate if a change in the LF/HF ratio indicative of cardiac ischemia is detected.

* * * * *